United States Patent [19]

Pfeiler et al.

[11] Patent Number: 5,293,416
[45] Date of Patent: Mar. 8, 1994

[54] RADIOGRAPHY APPARATUS FOR PRODUCING X-RAY SHADOWGRAPHS

[75] Inventors: Manfred Pfeiler; Paul Marhoff, both of Erlangen, Fed. Rep. of Germany

[73] Assignee: Siemens Aktiengesellschaft, Munich, Fed. Rep. of Germany

[21] Appl. No.: 977,055

[22] Filed: Nov. 16, 1992

[30] Foreign Application Priority Data

Jan. 13, 1992 [DE] Fed. Rep. of Germany ....... 4200653

[51] Int. Cl.$^5$ .............................................. G21K 5/10
[52] U.S. Cl. .......................................... 378/146; 378/4; 378/19
[58] Field of Search ...................... 378/146, 145, 4, 19

[56] References Cited

U.S. PATENT DOCUMENTS

4,179,100 12/1979 Sashin et al. .................. 378/146
4,442,489 4/1984 Wagner ........................... 378/19

FOREIGN PATENT DOCUMENTS

0166567 1/1986 European Pat. Off. .
3600221 7/1987 Fed. Rep. of Germany .
1558155 12/1979 United Kingdom .

OTHER PUBLICATIONS

"New Means for Picture Formation in Computer Tomography," Kowalski et al., Optik, vol. 55, No. 1 (1980), pp. 67–86.

"Die Digitale Bildetechnik in der Konventionellen Röntgendiagnostik: Bestandsaufnahme und Ausblick," Pfeiler et al., Electromedica vol. 52, No. 1, (1984) pp. 1–12.

"10 Jahre Computertomographie-ein Rückblick," Dümmling, Electromedica vol. 52, No. 1, (1984) pp. 13–27.

Primary Examiner—David P. Porta
Attorney, Agent, or Firm—Hill, Steadman & Simpson

[57] ABSTRACT

A radiography apparatus with which x-ray shadowgraphs are produced has a detector array in the form of a line or strip, and an x-ray radiator which is moved in a direction perpendicular to the line direction of the detector array for scanning a measuring field from different directions. The detector array accordingly receives x-radiation proceeding through the measuring field from different directions. A screen or slotted diaphragm having diaphragm shafts directed onto the detector array is disposed between the x-ray radiator and the measuring field, and blanks out x-radiation which is not useful for generating the shadowgraph image.

3 Claims, 2 Drawing Sheets

RADIOGRAPHY APPARATUS FOR PRODUCING X-RAY SHADOWGRAPHS

BACKGROUND OF THE INVENTION

1. Field of the Invention

The present invention is directed to an x-ray apparatus of the type used to produce an x-ray shadowgraph.

2. Description of the Prior Art

It is known to prepare x-ray shadowgraphs using a slotted diaphragm by scanning a line-shaped detector array with a fan-shaped x-ray beam, by causing the x-ray beam to move across a predetermined measurement field while also moving the detector array. An x-ray shadowgraph of a subject in the scanned measuring field can then be reconstructed from the electrical output signals of the detector array. A disadvantage of this known technique is that a relatively large number of mechanical parts must be moved in synchronism with each other, including at least the detector array as well as a slotted diaphragm for gating the x-ray beam. In order to retain an optimum anode angle in the image-effective beam path, the x-ray radiator is usually also moved, i.e., rotated.

SUMMARY OF THE INVENTION

It is an object of the present invention to provide a radiography apparatus with which x-ray shadowgraphs can be produced which permits an x-ray shadowgraph of a subject to be reconstructed in a predetermined measuring field with a minimum of mechanically moved components, while using a detector array.

The above object is achieved in a radiography apparatus which includes means for moving the x-ray source in a direction perpendicular to the line direction of the detector array, so that the detector array is irradiated by an x-ray beam which scans the measuring field from different directions. In the radiography apparatus disclosed herein, the only component which must be moved for scanning the x-ray field is the x-ray radiator. The detector array remains at rest.

In an embodiment of the invention, a screen or slotted diaphragm having diaphragm shafts aligned to the detector array is disposed preceding the measuring field in the direction of radiation propagation. This screen diaphragm assures that a fan-shaped x-ray beam is incident on the detector array for each measuring position of the x-ray radiator.

In a further embodiment of the invention, the radiography apparatus can be combined with or in a computer tomography apparatus, having a measuring unit consisting of an x-ray radiator and a CT detector array curved around the focus of the x-ray radiator. The measuring unit can be rotated around a system axis, and the detector array for generating the x-ray shadowgraphs is oriented perpendicularly to the CT detector array. In a computer tomography apparatus, the x-ray radiator is already capable of being mechanically moved in order to create computer tomograms. This same mechanical motion, and the structure for generating the mechanical motion, are used for preparing x-ray shadowgraphs in accordance with the principles of the present invention.

DESCRIPTION OF THE PREFERRED EMBODIMENTS

Figure 1:
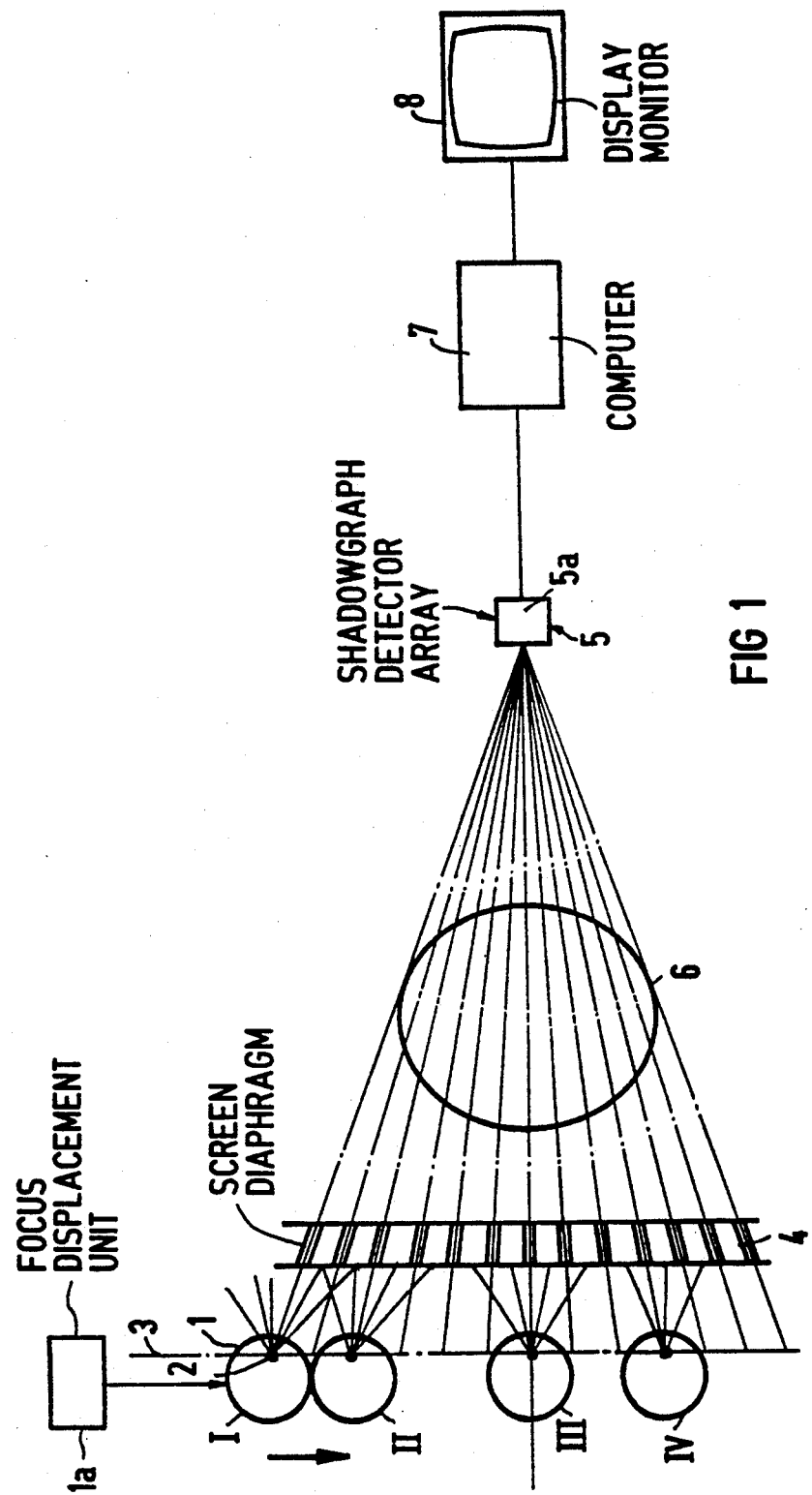
FIG. 1 is a schematic block diagram of a radiography apparatus constructed in accordance with the principles of the present invention.

A radiography apparatus for producing x-ray shadowgraphs, constructed in accordance with the principles of the present invention, is shown in FIG. 1. The apparatus includes an x-ray radiator 1 having a focus 2. The focus 2 is displaceable by a focus displacement unit 1a along a dot-dash line 3 in the direction of the arrow. In the embodiment of FIG. 1, the focus displacement unit 1a is shown as a unit for physically displacing the x-ray radiator 1.

The x-ray beam emanating from the focus 2 and emerging from the x-ray radiator 1 is gated by a stationary screen diaphragm 4, so that a fan-shaped x-ray beam is generated which is incident on a detector array 5 for each measuring position. The detector array 5 is formed by a row of detector elements extending perpendicularly relative to the plane of the drawing. Accordingly, one detector element 5a of the detector array 5 is visible in FIG. 1. Four of the plurality of different measuring positions of the x-ray radiator 1 are shown in FIG. 1, being referenced 1, 11, Ill and IV. As can be seen in FIG. 1, the diaphragm shafts of the screen diaphragm 4 are aligned onto the detector array 5.

As a result of mechanical movement of the x-ray radiator 1 in the direction of the arrow, a measuring field 6 is scanned, and a subject in the measuring field 6 is transirradiated by a fan-shaped x-ray beam from different directions. The fan plane of this x-ray beam proceeds perpendicular to the plane of the drawing. The detector elements 5a (and others) of the detector array 5 are all electrically connected to a computer 7, which calculates an x-ray shadowgraph of the subject in the measuring field 6 from the electrical output signals of the detector elements, corresponding to the intensity of the attenuated radiation thereon and effects the reproduction of the shadowgraph on a display monitor 8.

The screen diaphragm 4 blanks out radiation which is not effective for generating the shadowgraphed image before that radiation reaches the subject. The screen diaphragm 4 can alternatively be movable, i.e., it can be adjustable in direction of the arrow together with the x-ray radiator 1, in which case a single diaphragm shaft is sufficient.

Figure 2:
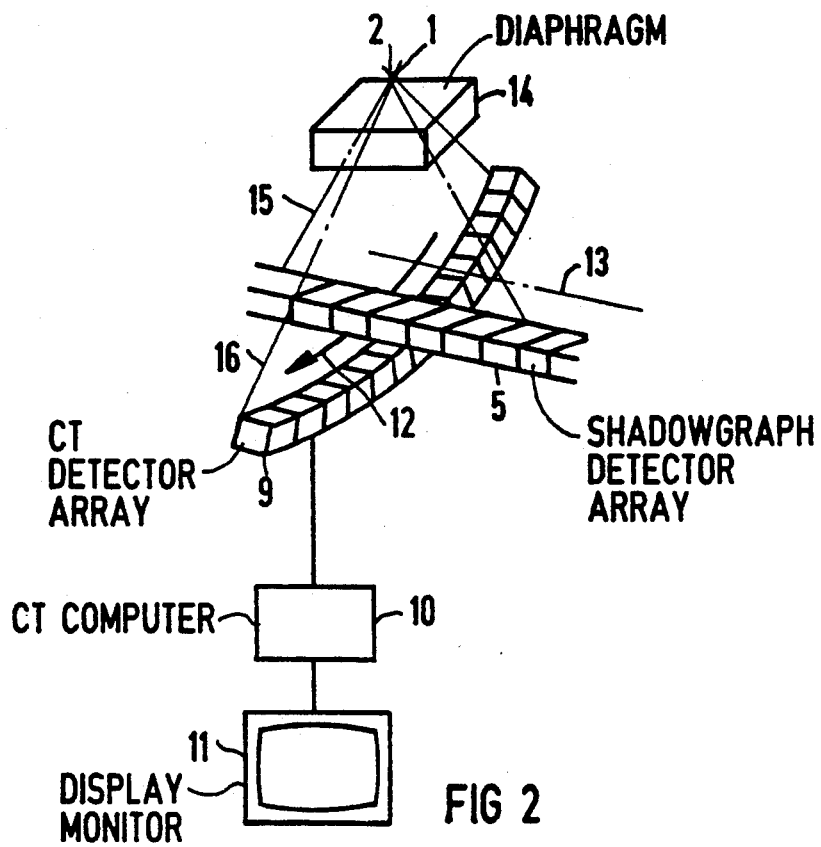
FIGS. 2 and 3 show the relevant components of a computer tomography apparatus with a radiography apparatus constructed in accordance with the principles of the present invention, as shown in FIG. 1, incorporated therein.

The radiography apparatus constructed in accordance with the principles of the present invention can be incorporated in a computer tomography apparatus. The components of a computer tomography apparatus for explaining the interaction with the radiography apparatus of the invention are shown in FIG. 2. These components include the focus 2 of an x-ray radiator (not separately shown) and a CT detector array 9, which is curved on a arc centered on the focus 2. The CT detector 9 is composed of a row of individual detector elements. For preparing computer tomograms, the measuring unit consisting of the x-ray radiator with the focus 2 and the CT detector array 9 is rotated around a system axis 13 in the direction of the arrow 12. A computer 10 calculates a computer tomogram of an examined slice of a subject from the output signals of the detector elements of the CT detector array 9. A visual reproduction of this computer tomogram is displayed on a monitor 11.

The detector array 5 for the production of x-ray shadowgraphs in accordance with the principles of the present invention is arranged perpendicularly to the CT detector array 9. The detector array 5 can be brought from a standby position to a position for preparing x-ray shadowgraphs, so that it does not represent a disturbing factor in the production of computer tomograms. The x-ray beam emanating from the focus 2 is gated using a diaphragm 14 for preparing x-ray shadowgraphs so that the detector array 5 is irradiated by a fan-shaped x-ray beam 15. For preparing computer tomograms, the diaphragm 14 gates the x-ray beam to produce a fan-shaped x-ray beam 16. The fan-shaped beam 16 is in a plane which is substantially perpendicular to the plane of the beam 15 used for preparing x-ray shadowgraphs.

For preparing an x-ray shadowgraph, only the x-ray radiator having the focus 2 is mechanically moved, so that a measuring field is penetrated by the fan-shaped x-ray beam 15 from different directions, as explained in connection with FIG. 1. The detector elements of the detector array 5 thus generate output signals which, as shown in FIG. 1, are processed by a computer 7 to form an x-ray shadowgraph which can be reproduced on a display 8.

Figure 3:
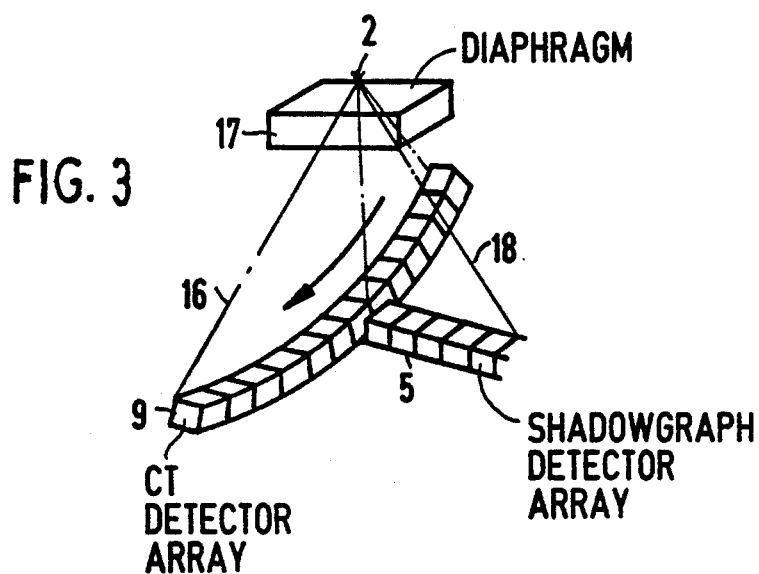

In the embodiment of FIG. 3, a diaphragm 17 is provided which, in addition to gating the fan-shaped x-ray beam 16 for the production of computer tomograms, can also gate a fan-shaped x-ray beam 18 for generating x-ray shadowgraphs. The fan-shaped x-ray beam 18, like the x-ray beam 15 in the embodiment of FIG. 2, is disposed perpendicularly relative to the plane of the x-ray beam 16, however, in contrast to the beam 15 of FIG. 2, the beam 18 is disposed laterally next to the plane of the x-ray beam 16. Consequently, the detector array 5 for preparing x-ray shadowgraphs also lies laterally next to the CT detector array 9. This results in the avoidance of the need to mechanically move the detector array 5 into position before the production of x-ray shadowgraphs.

The diaphragms 14 and 17 permit the gating of a fan-shaped x-ray beam 16 for the production of computer tomograms, and also permit gating, respectively, of the fan-shaped x-ray beams 14 and 18 proceeding in a plane perpendicularly to the plane in which the x-ray beam 16 is disposed.

The diaphragm 14 or 17 can also be moved along a circular arc, around a rotational axis lying in the detector array 5. In this case, only one stationary diaphragm for gating a fan-shaped x-ray beam having a single diaphragm aperture is sufficient.

Although modifications and changes may be suggested by those skilled in the art, it is the intention of the inventors to embody within the patent warranted hereon all changes and modifications as reasonably and properly come within the scope of their contribution to the art.

We claim as our invention:

1. A radiography apparatus for producing x-ray shadowgraphs comprising:
   an x-ray radiator having a focus from which an x-ray beam emanates;
   a detector array formed by a line of detector elements; and
   means for moving said x-ray radiator while said detector array remains stationary for transirradiating a measurement field, disposed between said x-ray radiator and said detector array, from different directions with said x-ray beam with said x-ray beam being incident on said detector array after passing through said measuring field from said different directions, said detector array generating electrical signals corresponding to the x-rays incident thereon;
   means for constructing an x-ray shadowgraph from said electrical signals;
   a computer tomography detector array curved around said focus of said x-ray radiator and forming, in combination with said x-ray radiator, a computer tomography measuring unit movable by said means for moving said x-ray radiator around a system axis, said detector array for producing x-ray shadowgraphs being disposed perpendicularly relative to said computer tomography detector array, said computer tomography detector array generating electrical signals corresponding to x-rays from said x-ray radiator incident thereon; and
   means for generating a computer tomogram from said electrical signals from said computer tomography detector array.

2. A radiography apparatus as claimed in claim 1 wherein said detector array for producing x-ray shadowgraphs is disposed above said computer tomography detector array.

3. A radiography apparatus as claimed in claim 1 wherein said detector array for producing x-ray shadowgraphs is disposed next to said computer tomography detector array.

* * * * *